United States Patent [19]

Becker et al.

[11] Patent Number: 5,256,687
[45] Date of Patent: Oct. 26, 1993

[54] PHARMACEUTICAL COMPOSITION FOR THE TREATMENT OF HIGH BLOOD PRESSURE

[75] Inventors: Reinhard Becker, Wiesbaden; Rolf Geiger, Frankfurt am Main; Rainer Henning, Hattersheim am Main; Volker Teetz, Holheim am Taunus; Hansjörg Urbach, Kronberg/Taunus, all of Fed. Rep. of Germany

[73] Assignee: Hoechst Aktiengesellschaft, Frankfurt am Main, Fed. Rep. of Germany

[21] Appl. No.: 979,390

[22] Filed: Nov. 19, 1992

Related U.S. Application Data

[63] Continuation of Ser. No. 776,699, Oct. 16, 1991, abandoned, which is a continuation of Ser. No. 519,026, May 4, 1990, abandoned, which is a continuation of Ser. No. 287,529, Dec. 19, 1988, abandoned, which is a continuation of Ser. No. 903,950, Sep. 5, 1986, abandoned.

[30] Foreign Application Priority Data

Sep. 9, 1985 [DE] Fed. Rep. of Germany ....... 3532036

[51] Int. Cl.$^5$ .................... A61K 31/40; A61K 31/405; A61K 31/34
[52] U.S. Cl. .................... 514/419; 514/415; 514/429; 514/471; 514/869
[58] Field of Search ............... 514/419, 412, 429, 869, 514/471

[56] References Cited

U.S. PATENT DOCUMENTS

| | | | |
|---|---|---|---|
| 4,217,347 | 8/1980 | Horovitz et al. | 424/246 |
| 4,374,829 | 2/1983 | Harris et al. | 424/177 |
| 4,564,625 | 1/1986 | Muschaweck et al. | 514/129 |

OTHER PUBLICATIONS

R. H. A. Becker et al., "Loop Diuretics Combined with an Ace Inhibitor for Treatment of Hypertension: A Study with Furosemide, Piretanide, and Ramipril in Spontaneously Hypertensive Rats", Journal of Cardiovascular Pharmacology, 1989, 13, pp. S35–S39.

Metzger et al., "2-[N-[(S)-1-Ethoxycarbonyl-3-phenylpropyl]-L-alanyl]-(1S, 3S, 5S)-2-azabicyclo[3.3.0]octane-3-carboxylic Acid (HOE498)—A New and Highly Effective Angiotension I Converting Enzyme Inhibitor", Drug Research, vol., 34 (II), NR. 10b, pp. 1402–1406 (1984).

Gavras et al., "Antihypertensive Effect of the New Oral Antiotension Converting Enzyme Inhibitor MK–421", The Lancet, Sep. 12, 1981, 543–546.

Lederle et al., "Antihypertensiver Effect des Converting-Enzym-Inhibitors Captopril bei essentieller Hypertonie", Therapiewoche 29, (1979), p. 7746.

Studer et al., "Captopril (SQ 14225) bei terapieresistenter Hypertonie", Terapiewoche 29, 45 (1979), p. 7749.

Vlasses et al. "Comparative Antihypertensive Effects of Enalapril Maleate And Hydrochlorothiazide, Along And In Combination", J. Clin. Pharmocol. 23:227–233 (1983).

Chem. Abst. 101, p. 35 (1984).

Patent Abstract of Japan, vol. 6, No. 24 (C–91)/902, Feb. 12, 1982.

MacGregor, et al., Captopril In Essential Hypertension: Contrasting Effects of Adding Hydrochlorothiazide or Propranolol, British Medical Journal. vol. 284, pp. 693–696 (Mar. 6, 1982).

(List continued on next page.)

Primary Examiner—Frederick E. Waddell
Assistant Examiner—T. J. Criares
Attorney, Agent, or Firm—Finnegan, Henderson, Farabow, Garrett & Dunner

[57] ABSTRACT

The invention relates to a pharmaceutical composition comprising an angiotensin converting enzyme inhibitor (trandolpril or pamipril) and a loop diuretic (Furosemide or piretanide), and to their use for the treatment of high blood pressure.

12 Claims, 1 Drawing Sheet

OTHER PUBLICATIONS

Chiu, et al., Acute Blood Pressure and Urinary Responses To Single Single Dose Combinations of Captopril and Diuretics In Conscious Spontaneously Hypertensive Rats, J. Pharm. Pharmacol., vol. 37, pp. 105–109 (1985).

Brunner et al., Enhancements By Diuretics Of The Antihypertensive Action of Long-Term Angiotensive Converting Enzyme Blockade. Clinical and Experimental Hypertension, vol. 2 (3&4), pp. 639–657 (1980).

Scholkens et al., Cardiovascular And Antihypertensive Activities Of The Novel Nonsulfhydryl Converting Enzyme Inhibitor 2-[N-υ(S)-1-Ethoxycarbonyl-3-phenylpropyl]-L-alanyl]-(1S, 3S, 5S) 2-azabicyclo [3.3.0] octane-3-carboxylic Acid (HOE-498), Drug Research, vol. 34 (II), NR. 10B, pp. 1417–1425 (1984).

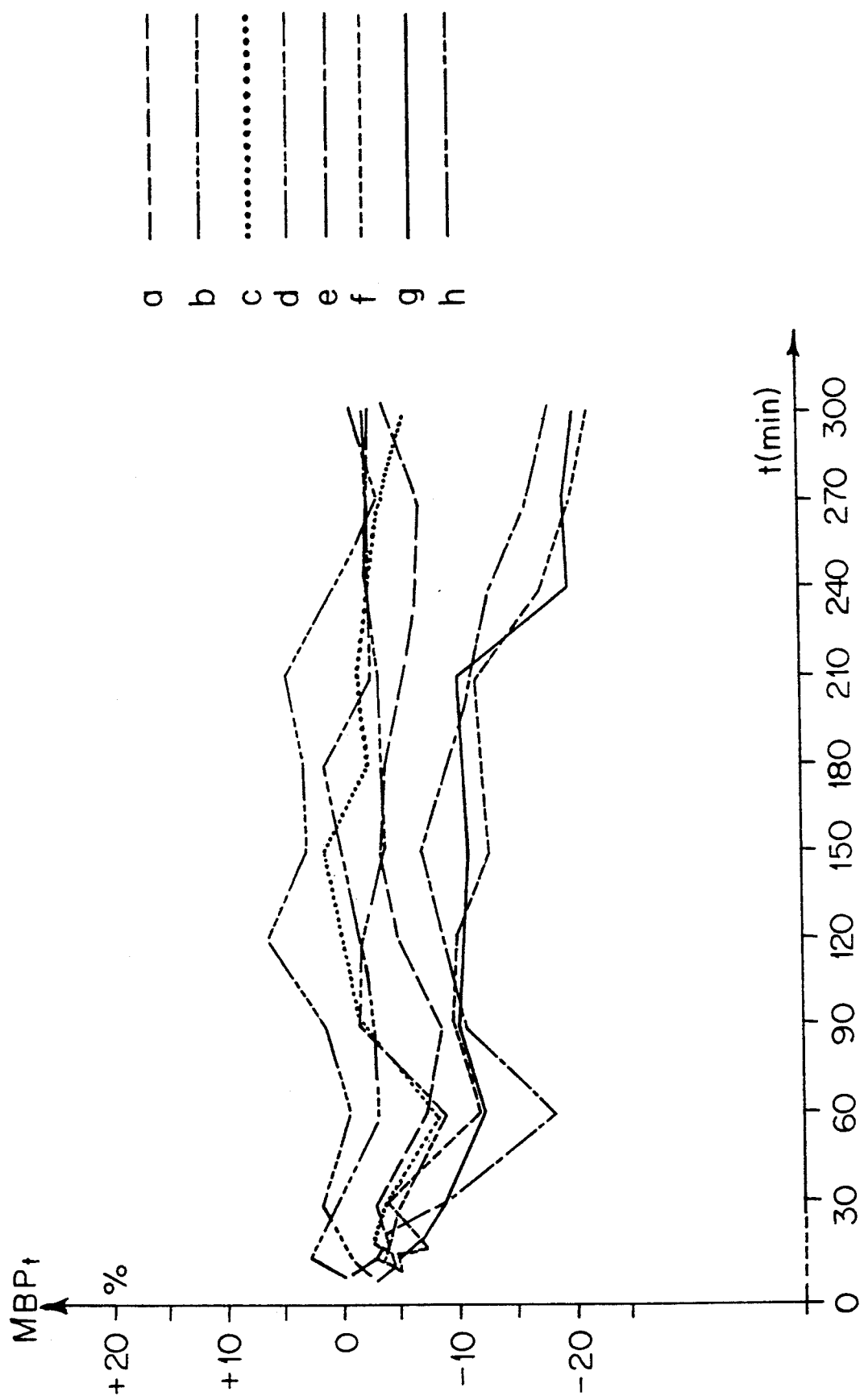

PHARMACEUTICAL COMPOSITION FOR THE TREATMENT OF HIGH BLOOD PRESSURE

This application is a continuation, of application Ser. No. 07/776,699 filed Oct. 16, 1991, now abandoned which is a continuation of application Ser. No. 07/519,026 filed May 4, 1990, now abandoned, which is a continuation of application Ser. No. 07/287,529, filed Dec. 19, 1988, now abandoned, which is a continuation of application Ser. No. 06/903,750 filed Sept. 5, 1986, now abandoned.

BACKGROUND

It is known that the high blood pressure of patients with essential hypertension can be reduced using inhibitors of angiotensin converting enzyme (ACE inhibitors), such as captoprit or enalapril (Therapiewoche 29 [1979] 7746; Lancet 2 [1981] 543-546). However, a certain percentage of patients with essential hypertension do not respond to substances of this type (Drug Devel. Eval. 4 [1980] 82-91).

It has been disclosed that the antihypertensive action of enalapril or captopril is potentiated by the addition of diuretically effective amounts of a diuretic of the thiazide type of analogous compounds (Brunner et al., Clin. Exp. Hypertension 2 [1980] 639-657; McGregor et al., Br. Med. J. 284 [1982] 693-696). It is generally assumed that this effect is based on stimulation by the diuretic of the renin-angiotensin system via a loss of salt and volume (P. J. S. Chiu et al., J. Pharm. Pharmacol. 37 [1985] 105).

There is a report in Arzneim.-Forsch./Drug Res. 34 (II) [1984] 1417-1425 of investigations into the cardiovascular action of 2-[N-[(S)-1-carboxy-3-phenylpropyl]-L-alanyl]-(1S,3S,5S)-2-azabicyclo[3.3.0]octane-3-carboxylic acid ("ramiprilate"). This entailed animals being pretreated with furosemide or piretanide for several days for the purpose of sodium depletion.

We have now found, surprisingly, that ACE inhibitors combined with loop diuretics in low dosage effectively lower blood pressure.

DESCRIPTION OF DRAWING

FIG. I - Illustrates the effect on blood pressure using compositions of the instant invention.

Thus the invention relates to pharmaceutical compositions containing a) an angiotensin converting enzyme inhibitor or its physiologically tolerated salt, and b) a loop diuretic or its physiologically tolerated salt.

Examples of loop diuretics included within the meaning of the present invention are furosemide, bumetanide, ethacrynic acid, etozolin and piretanide. As is evident from the name, the main point of attack of these diuretics, which have a short but potent effect, is the loop of Henle (cf. Mutschler, Arzneimittelwirkungen (Effects of drugs) 4th Edition, Stuttgart 1981, pages 486 and 487). Compounds of the formula I

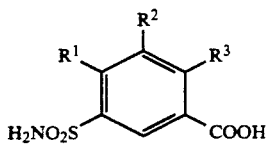

in which $R^1$ denotes chlorine or phenoxy, $R^2$ denotes hydrogen, pyrrolidino or n-butylamino, and $R^3$ denotes hydrogen or 2-furylmethylamino are particularly suitable examples.

Piretanide (see formula II)

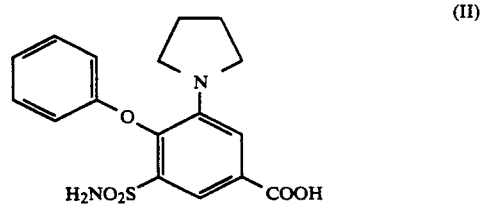

is particularly preferred.

Suitable ACE inhibitors are described in, for example, U.S. Pat. No. 4,129,571, U.S. Pat. No. 4,154,960, U.S. Pat. No. 4,374,829, European Patent A-79,522, European Patent A-79,022, European Patent A-49,658, European Patent A-51,301, U.S. Pat. No. 4,454,292, U.S. Pat. No. 4,374,847, European Patent A-72,352, U.S. Pat. No. 4,350,704, European Patent A-50,800, European Patent A-46,953, U.S. Pat. No. 4,344,949, European Patent A-84,164, U.S. Pat. No. 4,470,972, European Patent A-65,301 and European Patent A-52,991.

A large proportion of the ACE inhibitors disclosed in the abovementioned publications can be described by the general formula V,

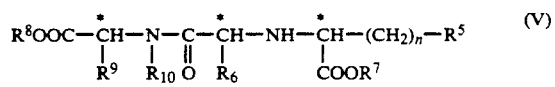

in which n is 1 or 2, $R^5$ denotes hydrogen, an optionally substituted aliphatic radial having 1-8 carbon atoms, an optionally substituted alicyclic radical having 3-9 carbon atoms, an optionally substituted aromatic radical having 6-12 carbon atoms, an optionally substituted araliphatic radical having 7-14 carbon atoms, an optionally substituted alicyclic-aliphatic radical having 7-14 carbon atoms, a radical $OR^a$ or $SR^a$, in which $R^a$ represents an optionally substituted aliphatic radical having 1-4 carbon atoms, represents an optionally substituted aromatic radical having 6-12 carbon atoms, or an optionally substituted heteroaromatic radical having 5-12 ring atoms, $R^6$ denotes hydrogen, an optionally substituted aliphatic radical having 1-6 carbon atoms, an optionally substituted alicyclic radical having 3-9 carbon atoms, an optionally substituted alicyclic-aliphatic radical having 4-13 carbon atoms, an optionally substituted aromatic radical having 6-12 carbon atoms, an optionally substituted araliphatic radical having 7-16 carbon atoms, an optionally substituted heteroaromatic radical having 5-12 ring atoms, or the side chain, protected where necessary, of a naturally occurring α-amino acid, R[7] and R[8] are identical or different and denote hydrogen, an optionally substituted aliphatic radical having 1-6 carbon atoms, an optionally substituted alicyclic radical having 3-9 carbon atoms, an optionally substituted aromatic radical having 6-12 carbon atoms, an optionally substituted araliphatic radical having 7-16 carbon atoms, and R[9] and R[10], together with the atoms carrying them, form a heterocyclic, mono-, bi- or tricyclic ring system having 3-15 carbon atoms, particularly suitable ring systems of this type being those of the following group:

Tetrahydroisoquinoline (A); decahydroisoquinoline (B); octahydroindole (C); octahydrocyclopenta[b]pyrrol (D); 2-azaspiro[4.5]decane (E); 2-azaspiro[4.4]nonane (F); spiro[(bicyclo[2.2.1]heptane)-2,3-pyrrolidine] (G); spiro[(bicyclo[2.2.2]octane)-2,3-pyrrolidine] (H); 2-azatricyclo[4.3.0.1[6,9]]decane (I); decahydrocyclohepta[b]pyrrol (J); octahydroisoindole (K); octahydrocyclopenta[c]pyrrol (L); 2,3,3a,4,5,7a-hexahydroindole (M); 2-azabicyclo[3.1.0]-hexane (N); all of which can optionally be substituted. However, the unsubstituted systems which have the following structural formulae are preferred.

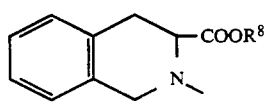 A

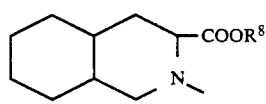 B

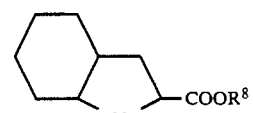 C

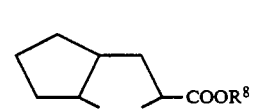 D

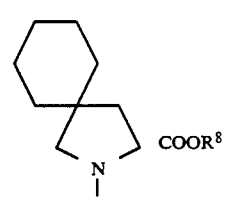 E

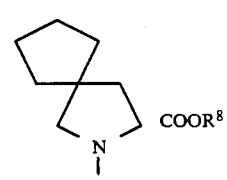 F

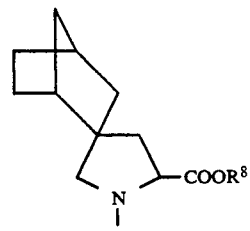 G

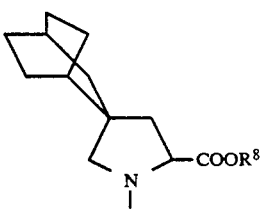 H

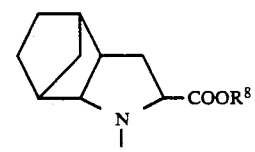 I

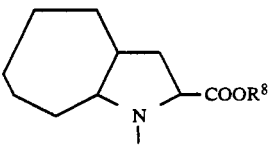 J

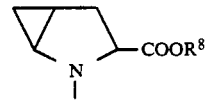 K

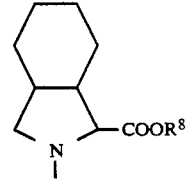 L

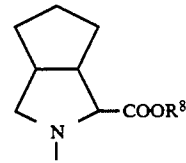 M

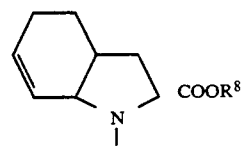 N

For the compounds which have several chiral atoms, all the possible diastereomers are suitable as racemates or enantiomers, or mixtures of various diastereomers. The S configuration of the carbon atoms labelled with an asterisk is preferred.

Examples of very suitable ACE inhibitors of the formula V are those in which n is 1 or 2, $R^5$ denotes hydrogen, alkyl having 1–8 carbon atoms, alkeny having 2–6 carbon atoms, cycloalkyl having 3–9 carbon atoms, aryl which has 6–12 carbon atoms and can be mono-, di- or trisubstituted by $(C_1-C_4)$-alkyl, $(C_1-C_4)$-alkoxy, hydroxyl, halogen, nitro, amino, aminomethyl, $(C_1-C_4)$-alkylamino, di- $(C_1-C_4)$-alkylamino, $(C_1-C_4)$-alkanaylamine, methylenedioxy, carboxyl, cyano and/or sulfamoyl, alkoxy having 1–4 carbon atoms, aryloxy which has 6–12 carbon atoms and can be substituted as described above for aryl, mono- or bicyclic heteroaryloxy which has 5–7 or 8–10 ring atoms respectively, 1 to 2 of these ring atoms being sulfur or oxygen atoms and/or 1–4 of these ring atoms being nitrogen, and which can be substituted a described above for aryl, Amino-$(C_1-C_4)$-alkyl, $(C_1-C_4)$-alkanoylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$-alkyl, $(C_6-C_{12})$-arylthio-$(C_1-C_4)$-alkyl which can be substituted in the aryl moeity as described above for aryl, $(C_6-C_{12})$-aryl-$(C_1-C_4)$-alkylthio which can be substituted in the aryl moeity as described above for aryl, carboxyl-$(C_1-C_4)$-alkyl, carboxyl, carbamoyl, carbamoyl-$(C_1-C_4)$-alkyl, $(C_1-C_4)$-alkoxycarbonyl-$(C_1-C_4)$-alkyl, $(C_6-C_{12})$-aryloxy-$(C_1-C_4)$-alkyl which can be substituted in the aryl moeity as described above for aryl, or $(C_6-C_{12})$-aryl-$(C_1-C_4)$-alkoxy which can be substituted in the aryl moeity as described above for aryl, $R^6$ denotes hydrogen, alkyl having 1–6 carbon atoms, alkenyl having 2–6 carbon atoms, alkynyl having 2–6 carbon atoms, cycloalkyl having 3–9 carbon atoms, cycloalkenyl having 5–9 carbon atoms, $(C_3-C_9)$-cycloalkyl-$(C_1-C_4)$-alkyl, $(C_5-C_9)$-cycloalkenyl-$(C_1-C_4)$-alkyl, optionally partially hydrogenated aryl which has 6–12 carbon atoms and can be substituted as described above for $R^5$, $(C_6-C_{12})$-aryl-$(C_1-C_4)$-alkyl or $(C_7-C_{13})$-aroyl-$(C_1$ or $C_2)$alkyl, each of which can be substituted as the preceding aryl, mono- or bicyclic, optionally partially hydrogenated heteroaryl which has 5–7 or 8–10 ring atoms respectively, 1 to 2 of these ring atoms being sulfur or oxygen atoms and/or 1 to 4 of these ring atoms being nitrogen atoms, and can be substituted as the preceding aryl, or the optionally protected side chain of a naturally occurring α-amino acid $R^6$—CH(NH$_2$)—COOH, $R^7$ and $R^8$ are identical or different and denote hydrogen, alkyl having 1–6 carbon atoms, alkenyl having 2–6 carbon atoms, di-$(C_1-C_4)$-alkylamino-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, aryl having 6–12 carbon atoms, $(C_6-C_{12})$-aryl-$(C_1-C_4)$-alkyl, $(C_3-C_9)$-cycloalkyl or $(C_3-C_9)$-cycloalkyl-$(C_1-C_4)$-alkyl and $R^9$ and $R^{10}$ have the abovementioned meaning, preferably those ACE inhibitors of the formula V in which n is 1 or 2, $R^5$ denotes $(C_1-C_6)$-alkyl, $(C_2-C_6)$-alkenyl, $(C_3-C_9)$-cycloalkyl, amino-$(C_1-C_4)$-alkyl, $(C_2-C_5)$-acylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy or 3-indolyl, in particular methyl, ethyl, cyclohexyl, tert.-butoxycarbonylamino-$(C_1-C_4)$-alkyl, benzoyloxycarbonylamino-$(C_1-C_4)$-alkyl or phenyl which can be mono- or disubstituted, or in the case of methoxy trisubstituted, by phenyl, $(C_1-C_2)$-alkyl, $(C_1$ or $C_2)$-alkoxy, hydroxyl, fluorine, chlorine, bromine, amino, $(C_1-C_4)$-alkylamino, di-$(C_1-C_4)$-alkylamino, nitro and/or methylenedioxy, $R^6$ denotes hydrogen or $(C_1-C_6)$-alkyl which can optionally be substituted by amino, $(C_1-C_6)$-acylamino or benzoylamino, $(C_2-C_6)$-alkenyl, $(C_3-C_9)$-cycloalkyl, $(C_5-C_9)$-cycloalkenyl, $(C_3-C_7)$-cycloalkyl-$(C_1-C_4)$-alkyl, $(C_6-C_{12})$-aryl or partially hydrogenated aryl, each of which can be substituted by $(C_1-C_4)$-alkyl, $(C_1$ or $C_2)$-alkoxy or halogen, $(C_6-C_{12})$-aryl-$(C_1$ to $C_4)$-alkyl or $(C_7-C_{13})$-aroyl-$(C_1-C_2)$-alkyl, both of which can be substituted in the aryl radical as defined above, a mono- or bicyclic heterocycle radical having 5 to 7 or 8 to 10 ring atoms respectively, 1 to 2 of these ring atoms being sulfur or oxygen atoms and/or 1 to 4 of these ring atoms being nitrogen atoms, or a side chain of a naturally occurring, optionally protected, α-amino acid, but in particular hydrogen, $(C_1-C_3)$-alkyl, $(C_2$ or $C_3)$-alkenyl, the optionally protective side chain of lysine, benzyl, 4-methoxybenzyl, 4-ethoxybenzyl, phenethyl, 4-aminobutyl or benzoylmethyl, $R^7$ and $R^8$ denote identical or different radicals hydrogen, $(C_1-C_6)$-alkyl, $(C_2-C_6)$-alkenyl or $(C_6-C_{12})$-aryl-$(C_1-C_4)$-alkyl, but in particular hydrogen, $(C_1-C_4)$-alkyl or benzyl, and $R^9$ and $R^{10}$ have the abovementioned meaning, in particular those ACE inhibitors of the formula V in which n is 2, $R^5$ denotes phenyl, $R^6$ denotes methyl, $R^7$ and $R^8$ denote identical or different $(C_1-C_6)$-alkyl radicals or $(C_7-C_{10})$-aralkyl radicals such as benzyl or nitrobenzyl, and $R^9$ and $R^{10}$ together represent a radical of the formula

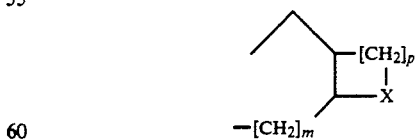

in which m denotes 0 or 1, p denotes 0, 1 or 2, and X denotes —CH$_2$—, —CH$_2$—CH$_2$— or —CH=CH—, it also being possible for a 6-ring formed with X to be a benzene ring.

Here and hereinafter, aryl is to be understood preferably to be optionally substituted phenyl, biphenylyl or naphthyl. A similar statement applies to radicals derived from aryl, such as aryloxy and arylthio. Aroyl is particularly understood to be benzoyl. Aliphatic radicals can be straight-chain or branched.

A mono- or bicyclic heterocycle radical having 5 to 7 or 8 to 10 ring atoms respectively, 1 to 2 of these ring atoms being sulfur or oxygen atoms and/or 1 to 4 of these ring atoms being nitrogen atoms, is understood to be, for example, thienyl, benzo|b|thienyl, furyl, pyranyl, benzofuryl, pyrrolyl, imidazolyl, pyrazolyl, pyridyl, pyrimidinyl, pyridazinyl, indzolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. It is also possible for the radicals to be partially or completely hydrogenated.

Naturally occurring α-amino acids are described in, for example, Houben-Weyl, Methoden der Organischen Chemie (Methods of Organic Chemistry), vol. XV/1 and XV/2. If $R^1$ represents a side chain of a protected naturally occurring α-amino acid such as, for example, protected Ser, Thr, Asp, Asn, Glu, Gln, Arg, Lys, Hyl, Cyc, Orn, Cit, Tyr, Trp, His or Hyp, preferred protective groups are the groups customary in peptide chemistry (cf. Houben-Weyl, vol. XV/1 and XV/2). In the case where $R^1$ denotes the protected side chain of lysine, the known amino protective groups are preferred, but in particular Z, Boc or $(C_1-C_6)$-alkanoyl. 0-protective groups suitable for tyrosine are preferably $(C_1-C_6)$-alkyl, in particular methyl or ethyl.

ACE inhibitors of the formula V can be prepared by reacting together their fragments in a suitable solvent, where appropriate in the presence of a base and/or of a coupling auxiliary, where appropriate reducing unsaturated compounds which are produced as intermediates, such as Schiff's bases, and eliminating protective groups which have been temporarily introduced for the protection of reactive groups, and converting the resulting compounds, where appropriate, into their physiologically tolerated salts.

It is possible to react compounds of the formula VI with compounds of the formula VII in the said manner.

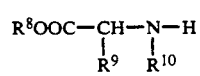

(VI)

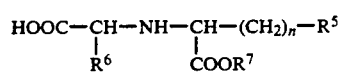

(VII)

The reaction of these compounds can be carried out, for example, in analogy to known peptide coupling processes in the presence of coupling auxiliaries such as carbodimides (for example dicyclohexylcarbodiimide), diphenylphosphoryl azide, alkanephosphoric anhydrides, dialkylphosphinic anhydrides or N,N-succinimidyl carbonates in $CH_3CN_9$Amino groups in compounds of the formula VI can be activated with tetraethyl diphosphite. The compounds of the formula VII can be converted into active esters (for example with 1-hydroxybenzotriazole), mixed anhydrides (for example with chloroformic esters), azides or carbodiimide derivatives, and thus be activated (cf. Schröder, Lübke, The Peptides, volume 1, New York 1965, pages 76-136).

It is likewise possible to react compound of the formula VII' with compounds of the formula VIII with the formation of compounds of the formula V,

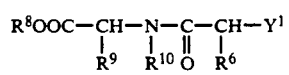

(VII')

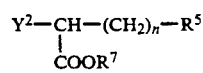

(VIII)

in which either $Y^1$ represents amino and $Y^2$ represents a leaving group, or $Y^1$ represents a leaving group and $Y^2$ represents amino. Examples of suitable leaving groups are Cl, Br, I, alkylsulfonyloxy of arylsulfonyloxy. Alkylations of this type are advantageously carried out in water or in an organic solvent in the presence of a base.

Furthermore, compounds of the formula IX can be condensed with compounds of the formula X

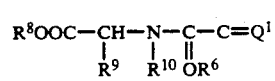

(IX)

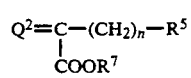

(X)

in which either $Q^1$ represents amino + hydrogen and $Q^2$ represents oxo, or $Q^1$ represents oxo and $Q^2$ represents amino + hydrogen. The condensation is advantageously carried out in water or in an organic solvent such as a lower alcohol, in the presence of a reducing agent, such as $NaBH_3CN$, compounds of the formula V being obtained directly. However, it is also possible to reduce the Schiff's bases or enamines produced as intermediates, where appropriate after previous isolation, with the formation of compounds of the formula V, for example by hydrogenation in the presence of a transition metal catalyst.

Finally, reaction of compounds of the formula IX ($Q^1=H+NH_2$) with compounds of the formula XI, or their reaction with compounds of the formulae XII and XIII, also result in compounds of the formula V (n=2),

(XI)

(XII)

(XIII)

the Schiff's bases produced as intermediates being reduced, and a carbonyl group being converted into methylene by reduction.

In the abovementioned formulae VI-XIII, $R^5-R^{10}$ and n are as defined in formula V. Protective groups introduced temporarily to protect reactive groups not involved in the reaction are eliminated in a manner know per se after the reaction is complete (cf. Schröder, Lübke, Loc. cit., pages 1-75 and 246-270).

Orally active ACE inhibitors are advantageous, such as, for example, ramipril, enalapril, captopril, lisinopril, perindopril, cilazapril, RHC 3659, CGS 13945, CGS 13928C, CGS 14824A, CI-906, SCH 31846, zofenopril, fosenopril, alaceptril and others. Orally active ACE inhibitors are described in, for example, Brunner et al., J. Cardiovasc. Pharmacol. 7 (Suppl. I) [1985] S2-S11.

The ACE inhibitors of the formula III

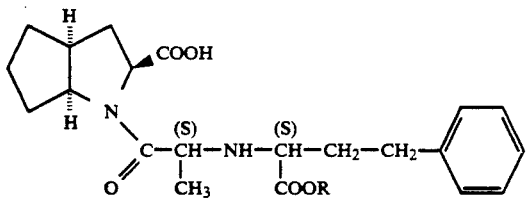

in which

R denotes hydrogen, ethyl, ethyl or benzyl, which are disclosed in European Patent A-79,022 are preferred, in particular the compound of the formula III in which R denotes ethyl (ramipril).

The ACE inhibitors of the formula IV

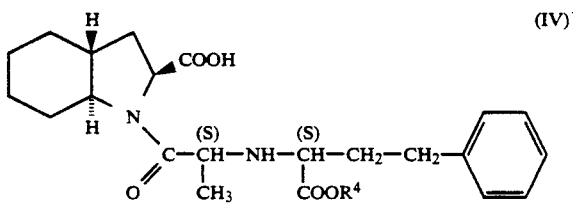

in which $R^4$ denotes hydrogen, $(C_1-C_4)$-alkyl or benzyl, which are disclosed in European Patent A-84,164, are also preferred, in particular the compound of the formula IV in which $R^4$ denotes ethyl.

Thus, preferred compositions according to the invention are those which contain a compound of the formula IV with $R^4$=ethyl together with piretanide or furosemide, but in particular those which contain ramipril together with piretanide and which contain ramipril together with furosemide.

The combination of ACE inhibitors and loop diuretics effects a potent and persistent lowering of blood pressure and can thus be used for the treatment of high blood pressure of various etiologies. It is a particularly interesting fact that there is not an additive behavior of the actions of the two components; on the contrary, a synergistic effect is observed. In spontaneously hypertensive rats there is a lowering of blood pressure with the combination even when it contains doses of an ACE inhibitor, such as ramipril, which alone have no effect, when they are combined with doses of a loop diuretic, such as piretanide, which alone have no diuretic effect (subdiuretic doses). This shows that loop diuretics, in particular compounds of the abovementioned formula I, are able to stimulate the renin-angiotensin system without showing a diuretic and saturetic effect. No such effect is achieved with compounds of the hydrochlorothiazide type.

For the reasons mentioned, the composition according to the invention is superior to the individual components for the treatment of high blood pressure, since it allows smaller doses of the components to be administered, and thus reduces any toxicological problems there may be.

The invention also relates to a process for the preparation of a composition of this type, which comprises conversion into a suitable form for administration of a) an angiotensin converting enzyme inhibitor or its physiologically tolerated salt, and b) a loop diuretic or its physiologically tolerated salt, together with physiologically acceptable vehicles and, where appropriate, other auxiliaries or additives.

The invention furthermore relates quite generally to products containing a) an angiotensin converting enzyme inhibitor or its physiologically tolerated salt, and b) a loop diuretic or its physiologically tolerated salt, preferably in a subdiuretic dose, as a combination product for concurrent, separate or sequential administration for the treatment of high blood pressure.

The ratio by weight of ACE inhibitor: loop diuretic in the said compositions and products varies depending on the activity of the active compounds, preferably between 10:1 and 1:500. For ramiprit (=A) + piretanide (=B), for example, A:B preferably varies between 4:1 and 1:10, in particular between 2:1 and 1:3. In contrast, with ramiprit (=A) + furosemide (=C) the ratio A:C is preferably 1:1 to 1:200, in particular 1:4 to 1:40.

By reason of their $pK_a$ value the loop diuretics of the formula I ($pK_a$ of furosemide: 3.8) form salts with ACE inhibitors of the formula V, the compound of the formula I being converted into its cation with protonation of the NH group adjacent to $CHR^6$ in the compound of the formula V. If the compound of the formula V ($R^7$ and/or $R^8$=H) is in the form of a zwitterion, a carboxylate group is protonated.

Hence the invention also relates to a salt of a loop diuretic of the formula I with an ACE inhibitor, and to pharmaceutical compositions and products which contain such a salt of a compound of the formula V. If necessary, the said compositions and products can additionally contain a loop diuretic of the formula I in the free form, or its physiologically tolerated salt, or a ACE inhibitor in the free form, or its physiologically tolerated salt.

Preferred salts of compounds of the formula I are those with compounds of the formula III or IV, in particular those of piretanide or furosemide with ramipril or a compound of the formula IV with $R^4$=ethyl.

The salts of compounds of the formula I with compounds of the formula V are prepared by dissolving stoichiometric amounts of the reactants in a suitable solvent, and depositing the salts in solid form by concentration, cooling or addition of another solvent in which they are less soluble. The salts can be processed to give compositions or products in the manner described above.

The doses of the ACE inhibitor and of the loop diuretic in the compositions or products according to the invention are each preferably selected so that the ACE inhibitor and/or the loop diuretic would alone show no effect or not a full effect. Thus, a dose of the loop diuretics which is far below the $ED_{50}$, for instance at its threshold diuretic dose, suffices. The sufficient doses of the ACE inhibitors as components are those which are at approximately the minimum dose adequate for plasma ACE inhibition (for determination, see: Metzger et al., Arzneim.-Forsch./Drug Res. 34 (II), 1402, 1403); thus, they can be below those which are required for an acute lowering effect on blood pressure when an ACE inhibitor is used alone.

For the use according to the invention in mammals, preferably in humans, for example the doses of an ACE inhibitor of the abovementioned formula III or IV range, for example, from 0.05 to 2 mg/kg/day, and those of a diuretic of the abovementioned formula I range from 0.2 to 25 mg/kg/day.

The compositions or products according to the invention can be administered parenterally or orally. The oral administration form is preferred.

The pharmacologically utilizable combinations of the present invention and their salts can be used for the preparation of pharmaceutical products which contain an effective amount of the active substances together with vehicles, and which are suitable for enteral and parenteral administration. Use is preferably made of tablets or gelatin capsules which contain the active compounds together with diluents, for example lactose, dextrose, sucrose, mannitol, sorbitol, cellulose and/or glycine, and lubricants such as diatomateous earth, talc, stearic acid or its salts, such as magnesium or calcium stearate, and/or polyethylene glycol. Tablets likewise contain binders, such as magnesium aluminum silicate, starch, gelatin, tragacanth, methylcellulose, sodium carboxymethylcellulose and/or polyvinylpyrrolidone, and, if necessary, pigment, flavorings and sweeteners.

Injectable solutions are preferably isotonic aqueous solutions or suspensions which can be sterilized and may contain auxiliaries such as preservatives, stabilizing agents, wetting and/or emulsifying agents, solubilizers, salts to regulate the osmotic pressure and/or buffer substances.

The pharmaceutical products according to the invention, which may contain, if desired, further pharmacologically valuable substances, are prepared by, for example, conventional mixing, granulating and coating processes, and contain 0.1% to about 75%, preferably about 1% to about 50%, of the active compounds.

This entails the active compounds being mixed or dissolved together with the abovementioned auxiliaries and additives in a mixing device at 5°–50° C. and then, for example, compressed to form tablets or dispensed into gelatin capsules or ampoules.

The examples which follow serve to illustrate the present invention without the latter being restricted to them.

EXAMPLE 1

Effect of the combination of ramipril (=A) and piretanide (=B) on the spontaneously hypertensive rat 10 spontaneously hypertensive rats (Wistar-Kyoto) are attached to instruments and kept in metabolism cages during the tests. Ramipril (=A) (1 mg/kg) and piretanide (=B) (1.2 and 16 mg/kg) are administered orally in Tylose using a stomach tube. The control group received only Tylose. The amount of urine excreted after 5 hours, the sodium excretion after 5 hours and the mean arterial pressure were determined.

TABLE 1

| Excretion of urine over 5 hours | |
|---|---|
| | Amount of urine (μL/100 g.5h) |
| Tylose (1 ml/kg) | 460 ± 65 |
| A (1 mg/kg) | 760 ± 185 |
| B (1 mg/kg) | 900 ± 180 |
| B (2 mg/kg) | 1470 ± 140 |
| B (16 mg/kg) | 3520 ± 405 |
| A (1 mg/kg) + B (1 mg/kg) | 1100 ± 145 |
| A (1 mg/kg) + B (2 mg/kg) | 1545 ± 130 |
| A (1 mg/kg) + B (16 mg/kg) | 3590 ± 285 |

TABLE 2

| Excretion of sodium over 5 hours | |
|---|---|
| | $m_{Na}(\bar{x} \pm SD \pm SEM)$ (mmol/150 g.5h) |
| Tylose (1 ml/kg) | 0.021 ± 0.0009 ± 0.003 |
| A (1 mg/kg) | 0.080 ± 0.049 ± 0.016 |
| B (1 mg/kg) | 0.082 ± 0.057 ± 0.021 |
| B (2 mg/kg) | 0.156 ± 0.063 ± 0.022 |
| B (16 mg/kg) | 0.462 ± 0.146 ± 0.052 |
| A (1 mg/kg) + B (1 mg/kg) | 0.157 ± 0.050 ± 0.321 |
| A (1 mg/kg) + B (2 mg/kg) | 0.158 ± 0.033 ± 0.012 |
| A (1 mg/kg) + B (16 mg/kg) | 0.513 ± 0.076 ± 0.031 |

The change in the mean blood pressure ($MBP_t$) as a % of the initial blood pressure ($MBP_0$) with time is shown in the figure. The individual lines in this figure have the following meanings:

Tylose (1 mg/kg): line h
A (1 mg/kg): line a
B (1 mg/kg): line b
B (2 mg/kg): line c
B (16 mg/kg): line d
A (1 mg/kg) + B (1 mg/kg): line g
A (1 mg/kg) + B (2 mg/kg): line f
A (1 mg/kg) + B (16 mg/kg): line e

EXAMPLE 2

Preparation of an oral combination product from ramipril (=A) and piretanide (=B)

1,000 tablets containing 1 mg of each of A and B were prepared using the following auxiliaries:

| A | 1 g |
|---|---|
| B | 1 g |
| Corn starch | 140 g |
| Gelatin | 7.5 g |
| Microcrystalline cellulose | 2.5 g |
| Magnesium stearate | 2.5 g |

A and B are mixed with an aqueous solution of gelatin. The mixture is dried and milled to form granules. Microcrystalline cellulose and magnesium stearate together with corn starch are mixed with the granules. The resulting granules are compressed to form 1,000 tablets, each tablet containing 1 mg of each of A and B.

EXAMPLE 3

Preparation of a parenteral combination product of ramipril (=A) and piretanide (=B)

The preparation of an injection solution for the treatment of hypertension is described below:

| A | 0.25 g |
|---|---|
| B | 0.25 g |
| Methyparaben | 5 g |
| Propylparaben | 1 g |
| Sodium chloride | 25 g |
| Water for injections | 5 l |

A, B, the preservatives and sodium chloride are dissolved in water for injection and made up to 5 L with water for injections. The solution is sterilized by filtration and dispensed under aseptic conditions into presterilized bottles which are closed with sterilized rubber caps. Each bottle contains 5 ml of solution.

EXAMPLE 4

Preparation of an oral combination product of ramipril (=A) and furosemide (=C)

1000 tablets which contain 5 mg of A and 20 mg of C were prepared with the following auxiliaries:

| | |
|---|---|
| A | 5 g |
| C | 20 g |
| Corn starch | 140 g |
| Gelatin | 7.5 g |
| Microcrystalline cellulose | 2.5 g |
| Magnesium stearate | 2.5 g |

A and C are mixed with an aqueous gelatin solution. The mixture is dried and milled to form granules. Microcrystalline cellulose and magnesium stearate together with corn starch are mixed with the granules. The resulting granules are compressed to form 1000 tablets, each tablet containing 5 mg of A and 20 mg of C.

EXAMPLE 5

Preparation of an oral combination product of enalapril (=D) and furosemide (=C)

1000 tablets containing 10 mg of b and 20 mg of C are prepared with the following auxiliaries:

| | |
|---|---|
| D | 10 g |
| C | 20 g |
| Corn Starch | 140 g |
| Gelatin | 7.5 g |
| Microcrystalline cellulose | 2.5 g |
| Magnesium stearate | 2.5 g |

D and C are mixed with an aqueous gelatin solution. The mixture is dried and milled to form granules. Microcrystalline cellulose and magnesium stearate together with corn starch are mixed with the granules. The resulting granules are compressed to form 1000 tablets, each tablet containing 10 mg of D and 20 mg of C.

EXAMPLE 6

In analogy to Example 2, tablets containing 4 mg of ramipril and 1 mg of piretanide per tablet are prepared.

EXAMPLE 7

In analogy to Example 2, tablets containing 0.5 mg of ramipril and 5 mg of piretanide per tablet are prepared.

EXAMPLE 8

In analogy to Example 4, tablets containing 25 mg of ramipril and 30 mg of furosemide per tablet are prepared.

EXAMPLE 9

In analogy to Example 4, tablets containing 1 mg of ramipril and 25 mg of furosemide per tablet are prepared.

We claim:

1. A pharmaceutical composition containing a synergistically effective amount of:
   (a) an angiotensin converting enzyme inhibitor, or its physiologically tolerated salt, of formula (III):

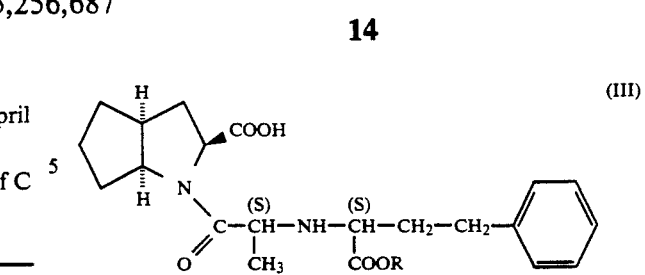

in which R denotes hydrogen, methyl, ethyl or benzyl, or of formula (IV):

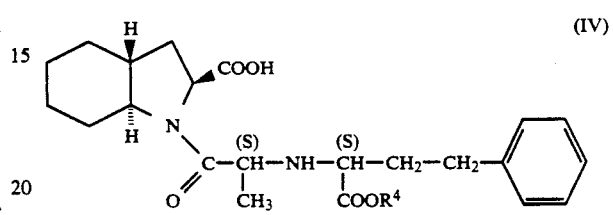

in which $R^4$ denotes hydrogen, $(C_1-C_4)$-alkyl or benzyl; and (b) a loop diuretic, or its physiologically tolerated salt, of formula (II) or of formula (II'):

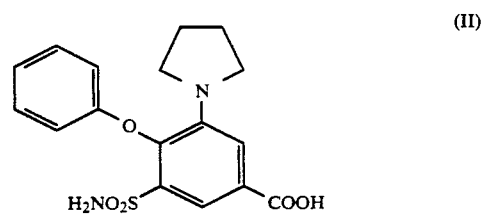

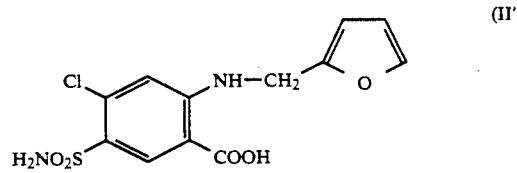

wherein said loop diuretic is present in a subdiuretic dose and wherein the combination of (a) and (b) is synergistically effective to lower blood pressure.

2. The pharmaceutical composition of claim 1, wherein R or $R^4$ denote ethyl.

3. The pharmaceutical composition of claim 1 wherein said angiotensin converting enzyme inhibitor is ramipril and said loop diuretic is the loop diuretic of formula (II).

4. The pharmaceutical composition of claim 1 wherein said angiotensin converting enzyme inhibitor is ramipril and said loop diuretic is the loop diuretic of formula (II').

5. The pharmaceutical composition of claim 1 wherein said angiotensin converting enzyme inhibitor is trandolapril and said loop diuretic is the loop diuretic of formula (II).

6. The pharmaceutical composition of claim 1 wherein said angiotensin converting enzyme inhibitor is trandolapril and said loop diuretic is the loop diuretic of formula (II').

7. A method for the treatment of high blood pressure in a mammal comprising the step of administering the pharmaceutical composition of claim 1.

8. A method for the treatment of high blood pressure in a mammal comprising the step of administering the pharmaceutical composition of claim 2.

9. A method for the treatment of high blood pressure in a mammal comprising the step of administering the pharmaceutical composition of claim 3.

10. A method for the treatment of high blood pressure in a mammal comprising the step of administering the pharmaceutical composition of claim 4.

11. A method for the treatment of high blood pressure in a mammal comprising the step of administering the pharmaceutical composition of claim 5.

12. A method for the treatment of high blood pressure in a mammal comprising the step of administering the pharmaceutical composition of claim 6.

* * * * *